(12) United States Patent
Adler et al.

(10) Patent No.: US 9,835,555 B2
(45) Date of Patent: *Dec. 5, 2017

(54) SENSOR FOR SENSING REFLECTIVE MATERIAL LOCATED ON A SURFACE HAVING MORE THAN ONE OF RADIATION EMITTERS LOCATED ON EITHER SIDE OF A RADIATION DETECTOR

(71) Applicants: Jeffrey Scott Adler, Beaconsfield (CA); Harold Russell Baird, Marietta, GA (US)

(72) Inventors: Jeffrey Scott Adler, Beaconsfield (CA); Harold Russell Baird, Marietta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/121,476

(22) Filed: Sep. 11, 2014

(65) Prior Publication Data

US 2016/0077002 A1    Mar. 17, 2016

(51) Int. Cl.
*G01N 21/55* (2014.01)
*G01N 21/94* (2006.01)
*B60S 1/08* (2006.01)

(52) U.S. Cl.
CPC ............ *G01N 21/55* (2013.01); *B60S 1/0833* (2013.01); *B60S 1/0837* (2013.01); *G01N 21/94* (2013.01); *G01N 2021/945* (2013.01); *G01N 2201/062* (2013.01)

(58) Field of Classification Search
CPC .............. B60R 1/0602; G01N 21/3554; G01N 2021/435; G01N 21/94; G01N 21/0303; G01N 21/55; G01N 21/6428; B60S 1/0833

USPC ..... 250/239, 216, 227.24, 227.25, 238, 573, 250/574; 318/483, DIG. 2; 340/555–557, 340/602–604

See application file for complete search history.

(56) References Cited

U.S. PATENT DOCUMENTS

| | | | |
|---|---|---|---|
| 3,801,779 A | 4/1974 | Ver Sluis | |
| 4,355,271 A | 10/1982 | Noak | |
| 4,432,645 A | 2/1984 | Frungel | |
| 4,701,613 A * | 10/1987 | Watanabe | ............. B60S 1/0822 250/227.24 |
| 4,960,996 A | 10/1990 | Hochstein | |
| 5,350,922 A | 9/1994 | Bartz | |
| 5,391,891 A | 2/1995 | Wiegleb et al. | |
| 6,084,519 A | 7/2000 | Coulling et al. | |
| 6,118,383 A | 9/2000 | Hegyl | |

(Continued)

FOREIGN PATENT DOCUMENTS

| | | |
|---|---|---|
| DE | 102006039034 | 2/2008 |
| EP | 1285830 A2 | 2/2003 |

(Continued)

*Primary Examiner* — Que T Le

(57) ABSTRACT

Described herein is a sensor for sensing reflective material. The sensor includes a housing with a transparent window and a sensor mount located in the housing and angled away from a housing wall. A radiation emitter is mounted in the sensor mount and emits radiation along an axis through the transparent window which has an amount of the reflective material located thereon. A radiation detector is mounted in the sensor mount and located adjacent the radiation emitter. The radiation detector is located to receive reflected radiation from the reflective material along another axis. The first axis is angled towards the second axis.

21 Claims, 5 Drawing Sheets

(56) References Cited

U.S. PATENT DOCUMENTS

| | | |
|---|---|---|
| 6,207,967 B1 | 3/2001 | Hochstein |
| 6,376,824 B1 | 4/2002 | Michenfelder et al. |
| 6,853,897 B2 | 2/2005 | Stam et al. |
| 7,847,255 B2 * | 12/2010 | Teder .................. B60S 1/0822 250/341.8 |
| 8,471,513 B2 | 6/2013 | Han |
| 2006/0076478 A1 | 4/2006 | Johnson et al. |

FOREIGN PATENT DOCUMENTS

| | | |
|---|---|---|
| EP | 2 236 954 A2 | 10/2010 |
| JP | 2004 0397753 A | 2/2004 |
| JP | 2011 009672 A | 1/2011 |
| WO | WO 2011/141892 | 5/2010 |

* cited by examiner

SENSOR FOR SENSING REFLECTIVE MATERIAL LOCATED ON A SURFACE HAVING MORE THAN ONE OF RADIATION EMITTERS LOCATED ON EITHER SIDE OF A RADIATION DETECTOR

CROSS-REFERENCE TO RELATED APPLICATION

The present is a continuation application of pending U.S. patent application Ser. No. 13/507,956, filed Aug. 9, 2012 to which priority is claimed under 35 U.S.C. §120, the entire contents of which are hereby incorporated by reference

TECHNICAL FIELD

The present relates to material sensors, and more particularly to a sensor for sensing reflective materials.

BACKGROUND

Precipitation sensors have been developed to determine the presence of water in its vapor, liquid and solid forms, but usually the sensor is immersed in the material. Non-immersed sensing is a significant challenge. One example of a non-immersed sensor is the Bosch vehicle windshield rain sensor (Optical Sensor U.S. Pat. No. 6,376,824 by Michenfelder et al) used to operate windshield wipers. This sensor depends on the change in refraction of a reflected light beam against glass when water is on the outer glass surface. However, it has poor sensitivity for snow, unless the glass can be heated enough to melt the snow next to the glass. This would be difficult to facilitate without making the vehicle occupants too uncomfortable and initially, in cold environments, would not work at all until the heating reached an acceptable level for the sensor to be engaged.

BRIEF SUMMARY

We have invented a sensor that uses a reflective rather than refractive technique, and as such is very well suited to determining the presence of winter precipitation such as snow, sleet, frost, ice or ice pellets. A radiation source such as a LED is oriented to radiate through a transparent material such as glass, at an angle that does not cause a surface reflection back to the radiation sensor. When a reflective material such as winter precipitation is on the transparent material surface, a radiation sensor such as but not limited to a photo transistor, photo diode or light dependent resister adjacent to the radiation source senses the radiation reflection.

Accordingly, there is provided a sensor for sensing reflective material, the sensor comprising:
 a housing having a transparent window;
 a sensor mount located in the housing and angled away from a housing wall;
 a radiation emitter mounted in the sensor mount for emitting radiation along a first axis through the transparent window, the transparent window having an amount of the reflective material located thereon; and
 a radiation detector mounted in the sensor mount and located adjacent the radiation emitter, the radiation detector being located to receive reflected radiation from the reflective material along a second axis, the first axis being angled towards the second axis.

In one example, the sensor includes two radiation emitters each located on either side of the radiation detector, the two radiation emitters being mounted to emit radiation along their respective first axes through the transparent window towards a common focal point on an outer surface of the transparent window. The sensor mount includes two spaced apart cavities aligned along the respective first axes in which the radiation emitters are located, and another cavity aligned along the second axis in which the radiation detector is located.

In one example, the sensor mount is located at a junction between the housing wall and a housing floor so that sensor mount is angled away from the housing wall.

In another example, a baffle extends into the housing from the housing wall.

In another example, a temperature sensor is located on a lower surface of the transparent window.

In yet another example, a baffle wall extends into the housing from the housing wall; and a temperature sensor is located on a lower surface of the transparent window.

In one example, the radiation emitter is a Light Emitting Diode (LED).

In one example, the radiation sensor is a photo transistor or photo diode located adjacent to the radiation emitter so as to detect reflected radiation.

In another example, the radiation emitter is disposed so that radiation is emitted through the transparent window at an angle that does not cause a surface reflection back to the radiation detector. A controller is located in the housing and is connected to a variable resistor, the radiation detector, the radiation emitter and the temperature sensor. A controller is located in the housing and is connected to a fixed resistor, the radiation detector, the radiation emitter and the temperature sensor.

In one example, the radiation detector is an integrated circuit having a photo transistor, a photo diode or a light dependent resister located adjacent to the radiation emitter so as to detect reflected radiation.

In another example, the reflective material is winter precipitation. The winter precipitation is snow, sleet, frost, ice or ice pellets.

In one example, the reflective material is non-winter precipitation: The non-winter precipitation is reflective liquids, dirt, or particulate material suspended in liquids.

In one example, the sensor is mounted for use on motorized transportation including trucks, cars, motor bikes, recreational vehicles, trains, or boats.

In another example, the sensor is mounted for use on solar panels and trough reflectors.

In yet another example, the sensor is mounted for use on sidewalks, driveways, walkways, roads, roofs, or infrastructure projects.

In another example, the sensor is mounted for use with greenhouses, atriums, windows, freezer glass doors, skylights; on planes, helicopters; food services, freezers/fridges, spacecraft, buildings; for landscaping such as grass and garden maintenance, crops; or for weather determination, climate, ecosystem preservation; or for medical applications and storage of tissues and cells, sterilizations; or for food preparation and preservation, and the like.

In another example, the sensor is used in solar applications for building materials including decking, walls or shingles.

BRIEF DESCRIPTION OF THE DRAWINGS

In order that the discovery may be readily understood, embodiments are illustrated by way of example in the accompanying drawings.

Further details of the device and its advantages will be apparent from the detailed description included below.

DETAILED DESCRIPTION

Figure 1:
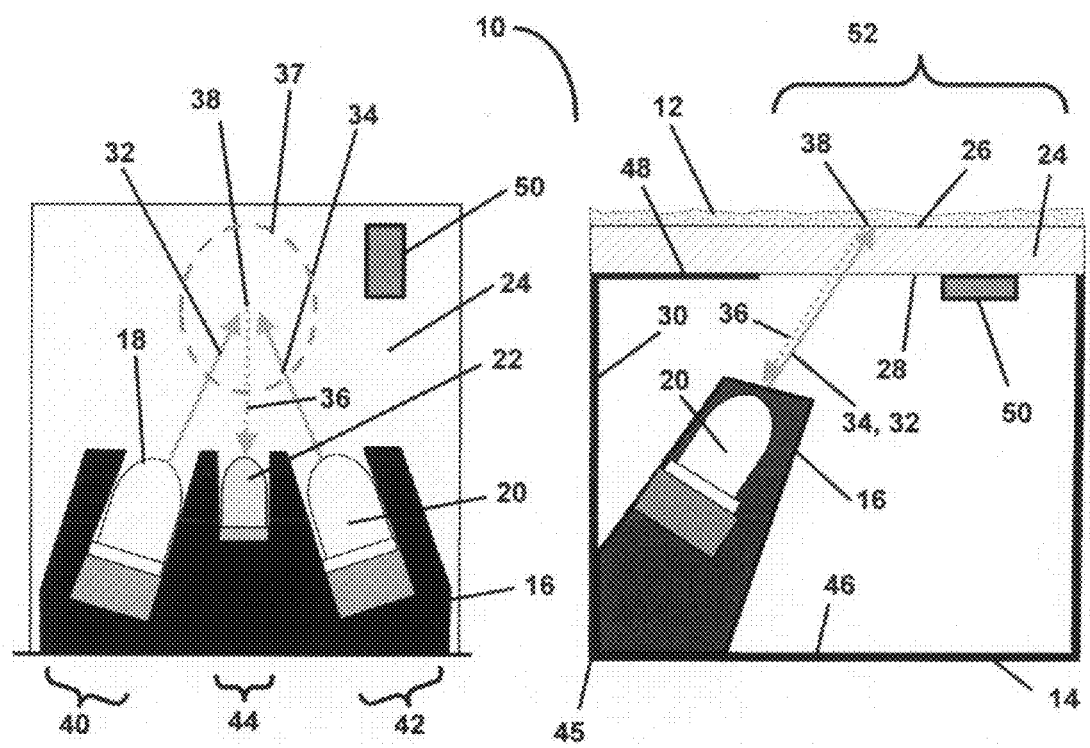
FIG. 1A illustrates top view of a sensor.
FIG. 1B illustrates a side view of the sensor showing radiation emitted and radiation reflected.
Figure 2:
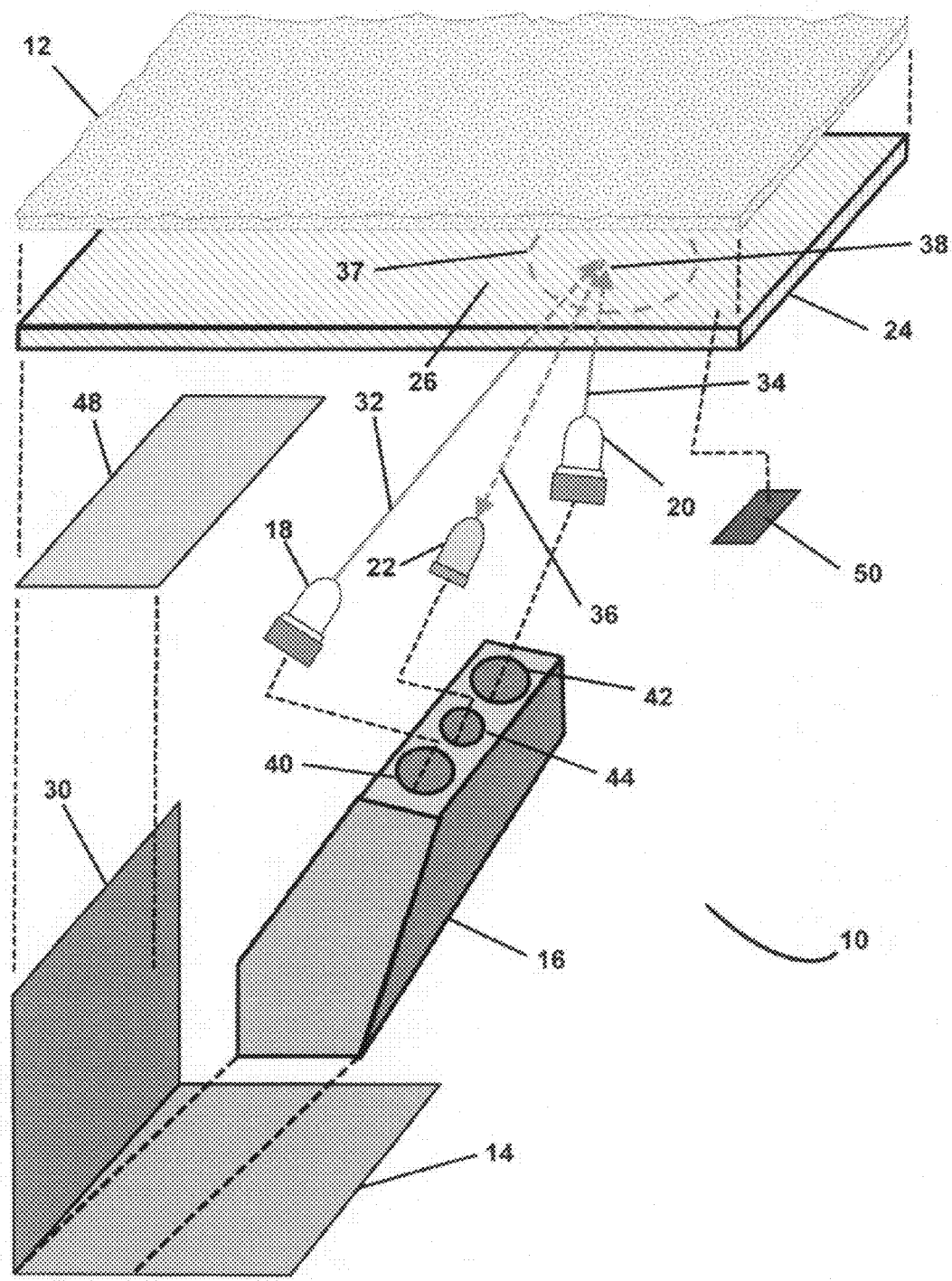
FIG. 2 illustrates an exploded view of the sensor.

Referring to FIGS. 1A, 1B and 2, there is illustrated generally at 10 a sensor for sensing reflective material 12. In one example, the reflective material is winter precipitation such as, for example, snow, frost, ice or ice pellets. In another example, the reflective material is non-winter precipitation such as reflective liquids, dirt, or particulate material suspended in liquids. Broadly speaking, the sensor 10 includes a housing 14, a sensor mount 16, two radiation emitters (radiation sources) 18, 20, and a radiation detector (radiation sensor) 22. The housing 14 has a transparent window 24 which includes an upper surface 26 and a lower surface 28 which is disposed towards the inside of the housing 14. The transparent window 24 has an amount of accumulated reflective material 12 located thereon. The sensor mount 16 is located in the housing 14 and angled away from a housing wall 30. The radiation emitters 18, 20 are mounted in the sensor mount 16. The radiation emitter 18, 20 each have a first axis 32, 34. Radiation is emitted from the radiation emitters 18, 20 along their respective axes 32, 34 towards and through the transparent window 24 until it contacts the reflective material 12. The radiation detector 22 is mounted in the sensor mount 16 and adjacent and between the radiation emitters 18, 20. The radiation detector 22 is located to receive the radiation that is reflected back from the reflective material 12 located on the transparent window 24 along a second axis 36. The first axes 32, 34 of the radiation emitters 18, 20 are both angled towards the second axis 36. The two radiation emitters 18, 20 emit radiation towards a common focal point 38 on the upper surface 26 of the transparent window 24 and at a deviation from normal such that their radiation is not mirror reflected to the radiation detector 22 from the upper or lower transparent window surfaces. The deviation from normal is also not large enough to cause all radiation to be to be reflected back into the housing 14. The radiation detector 22 is directed to the radiation emitter common focal point 38 on the upper surface of the transparent window.

Figure 3:
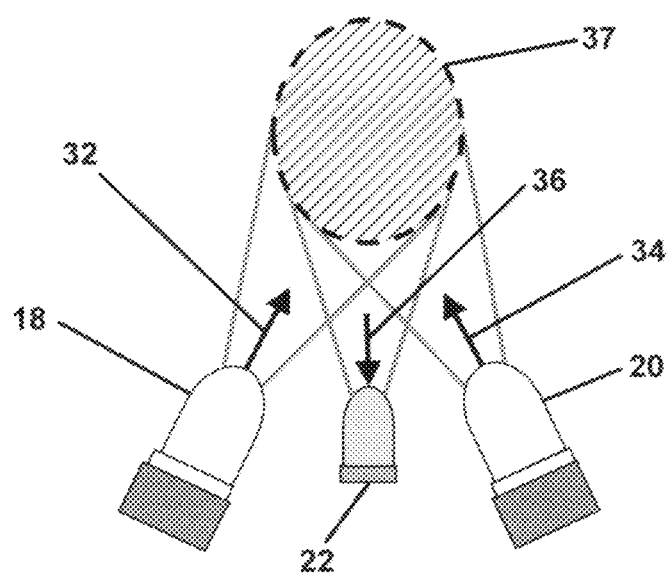
FIG. 3 illustrates the sensor's field of view.

Referring briefly to FIG. 3, radiation emitters 18 and 20 and radiation detector 22 have overlapping fields of useful radiation and detection to sense precipitation over area 37.

Still referring to FIGS. 1A, 1B and 2, the sensor mount 16 includes two spaced apart cavities 40, 42 which are both aligned along their respective first axes 32, 34 in which the radiation emitters 18, 20 are located. Another cavity 44 is aligned along the second axis 36 in which the radiation detector 22 is located.

As best illustrated in FIG. 1B, the sensor mount 16 is located at a junction 45 between the housing wall 30 and a housing floor 46 so that sensor mount 16 is angled away from the housing wall 30.

Still referring to FIG. 1B, a radiation baffle wall 48 extends into the housing 14 from the housing wall 30. The baffle wall 48 may be used to block external radiation sources such as the sun from the radiation detector 22. A temperature sensor 50 is located on the lower surface 28 of the transparent window 24 out of the radiation detector's 22 field of view, which will not cause a false reflection to the sensor. The baffle wall 48 can be constructed of any suitable shape to define the boundaries to radiation window 52 through which both the radiation from the radiation emitters 18, 20 and the radiation reflected back from the reflective material 12 passes.

Each of the radiation emitters is a Light Emitting Diode (LED). The radiation emitters 18, 20 are disposed so that radiation emitted through the transparent window 24 is at an angle that does not cause a surface reflection back to the radiation detector 22.

Figure 4:
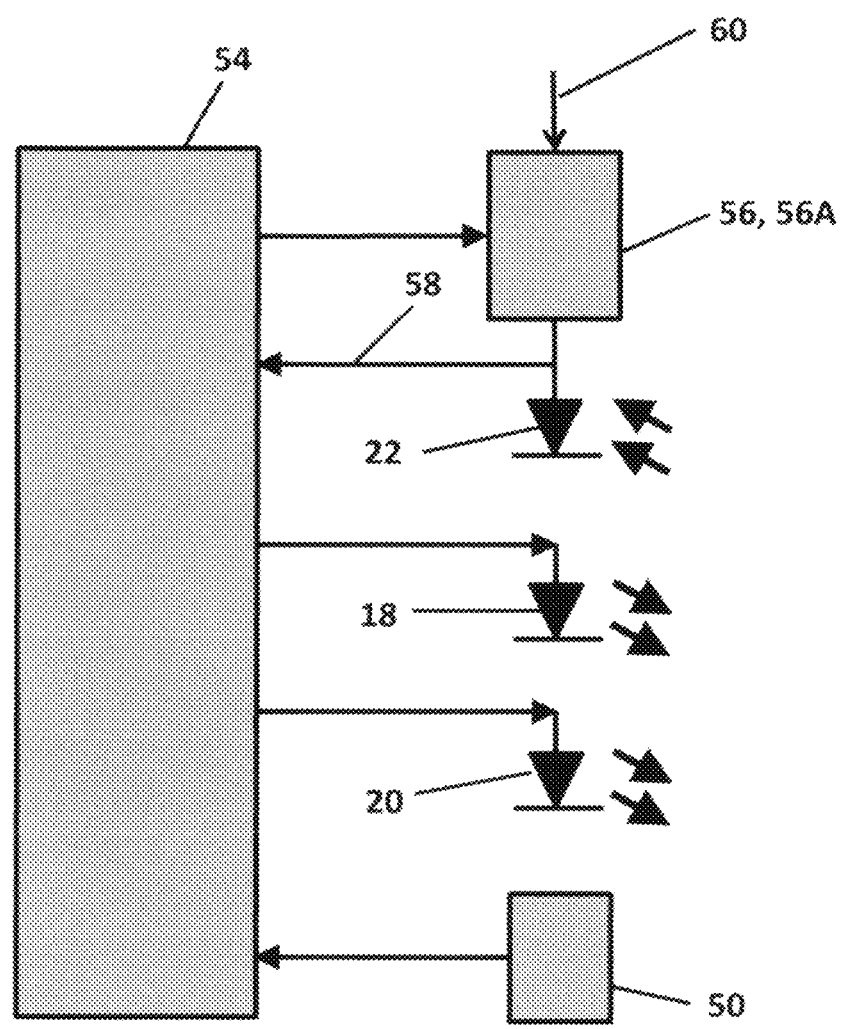
FIG. 4 is diagrammatic representation of communication between sensor components in one example of the sensor.

Referring now to FIG. 1, FIG. 2 and FIG. 4, a controller 54, which is typically a microprocessor or equivalent device, communicates with a variable resister 56 or fixed resister 56A, the radiation detector 22, the radiation emitters 18, 20 and the temperature sensor 50 to achieve the reflective material sensing function. The controller 54 may be located within the housing 14, or in another suitable housing. One skilled in the art will understand that other devices and circuitry such as cabling, voltage supply, ground, signal buffering, user communication, controller programming, and the like may also be integrated into the sensing function.

Referring now to FIG. 4, the radiation sensor 22 operates as an electrical current valve, which permits higher current flow at higher radiation levels. A radiation signal 58 is produced by passing a reference voltage 60 through the variable resister 56 and then the radiation detector. As radiation increases, the current flow through the radiation detector 22 increases, causing an increased voltage drop across the variable resister 56. To allow for a wide range of radiation, the controller 54 modifies the value of the variable resister 56 to produce a usable signal. For installations where the ambient radiation range is small, an inexpensive fixed resister 56A may be used, thereby eliminating the need for the controller 54 to modify the resister 56A value. Alternatively, more than one copy of a fixed but different value resister 56A and radiation sensor 22 may be used to broaden the sensed radiation range.

Figure 5:
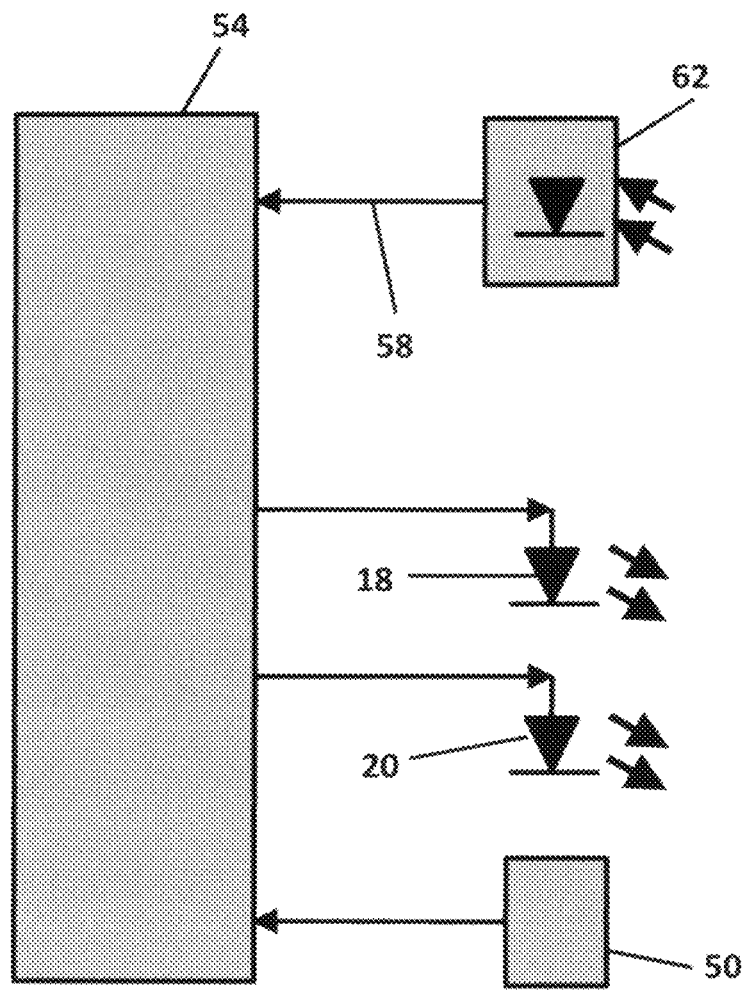
FIG. 5 is diagrammatic representation of communication between sensor components in an alternative example of the sensor.

Referring now to FIGS. 1, 2 and 5, the radiation sensor 22 is an integrated circuit 62 which includes a sensor such as a photo diode, photo transistor or light dependent resister and a means to autonomously convert the sensor output to the controller 54 compatible input such as frequency pulses.

Still referring to FIG. 4 or 5, the controller 54 activates one or both of the radiation emitters 18, 20 when required to achieve the sense function. To assist in distinguishing between winter and non-winter precipitation, the controller 54 communicates with the temperature sensor 50 to determine whether winter precipitation is possible.

The sensor 10 functions in a wide range of ambient radiations, from direct sunlight to nighttime. It can sense winter precipitation or cold precipitation on, for example, greenhouses, atriums, windows, freezer glass doors, skylights; on planes, helicopters, and motorized transportation including trucks, cars, motor bikes, recreational vehicles, trains, boats and the like; food services, freezers/fridges, spacecraft, buildings, photovoltaic solar (conventional panels and non conventional solar applications), trough reflectors; for landscaping such as grass and garden maintenance, crops; or for weather determination, climate, ecosystem preservation; or for medical applications and storage of tissues and cells, sterilizations; or for food preparation and preservation, and the like. When operated in non-winter conditions, the sensor 10 may also detect dirt on these types of surfaces to support cleaning operations. With a durable transparent cover, it can also sense winter precipitation when installed in sidewalks, driveways, walkways, roads, roofs, infrastructure projects and the like. The sensor 10 can be used in solar applications for building materials such as decking, walls and shingles.

While the sensor 10 can be used to sense winter precipitation, it is easily applied to sensing other reflective materials such as, for example, liquids, precipitates, contamination, some gases, suspended solids, and the like, and as such can be applied to manufacturing and distribution processes for food, chemicals, fuels, and the like.

Operation

Referring now to FIG. 1 and FIG. 4, operation of the sensor 10 will be described. Winter precipitation is sensed by determining the change in the radiation signal 58 when the radiation emitters 18, 20 are "off" then "on". Firstly, the controller 54 determines if winter precipitation is possible by communicating with the temperature sensor 50. If winter precipitation is possible, then the controller 54 determines a reference ambient radiation signal 58 by first not switching on the radiation emitters 18, 20, then modifying the variable resister 56 until the radiation signal 58 is approximately 90% of the reference voltage 60. The controller 54 determines the reference ambient radiation by comparing the resultant variable resister 56 resistance with internally stored data. If the fixed resister 56A is used, the controller 54 determines reference ambient radiation by comparing the radiation signal 58 with internally stored data.

Referring now to FIG. 5, an alternative operation of the sensor 10 will now be described. Winter precipitation is sensed by determining the change in the radiation signal 58 when the radiation emitters 18, 20 are "off" then "on". Firstly, the controller 54 determines if winter precipitation is possible by communicating with the temperature sensor 50. If winter precipitation is possible, then the controller 54 determines a reference ambient radiation signal by first not switching on the radiation emitters 18, 20 then communicating with the radiation detector 62.

Referring now to FIGS. 4 and 5, the controller 54 then turns on one or both of the radiation emitters, depending on the ambient radiation. At high ambient radiation, both radiation emitters 18, 20 may be required to obtain an adequate change in the radiation signal 58. The controller 54 then determines that winter precipitation is present if the radiation signal 58 value has changed from the reference ambient radiation signal value by more than the combined effect of impurities in the transparent window 24 and expected dirt on the transparent window 24. The controller 54 may also determine the type of winter precipitation based on the combination of the temperature sensor 50 and the radiation signal 58 change.

When used in non-winter precipitation mode to sense other materials, the temperature sensor 50 can be eliminated, or used to distinguish between winter precipitation and non-winter reflective material such as accumulating grime.

Although the above description relates to a specific preferred embodiment as presently contemplated by the inventor, it will be understood that the WPS in its broad aspect includes mechanical and functional equivalents of the elements described herein.

We claim:

1. A sensor for sensing reflective material, the sensor comprising:

a housing having a transparent window;

a sensor mount located in the housing and angled away from a housing wall;

one or more radiation emitters mounted in the sensor mount for emitting radiation along a first axis through the transparent window, the transparent window having an amount of the reflective material located thereon; and a radiation detector mounted in the sensor mount and located adjacent the one or more radiation emitters, the radiation detector being located to receive reflected radiation, when an amount of the reflective material is present, from the reflective material along a second axis, the first axis being angled towards the second axis;

the one or more radiation emitters for emitting radiation along the first axis to a surface of the transparent window, the surface of the transparent window causing a radiation reflection along a third axis, the third axis being angled away from the first axis and the second axis;

wherein more than one of the radiation emitters are located on either side of the radiation detector where each of the radiation emitters respective first axis is acutely angled towards the second axis, the one or more radiation emitters being mounted to emit radiation along their respective first axes through the transparent window towards a common focal point on an outer surface of the transparent window.

2. The sensor, according to claim 1, includes two radiation emitters each located on either side of the radiation detector, the two radiation emitters being mounted to emit radiation along their respective first axes through the transparent window towards the common focal point on the outer surface of the transparent window.

3. The sensor, according to claim 2, in which the sensor mount includes two spaced apart cavities aligned along the respective first axes in which the radiation emitters are located, and another cavity aligned along the second axis in which the radiation detector is located.

4. The sensor, according to claim 1, in which the sensor mount is located at a junction between the housing wall and a housing floor so that sensor mount is angled away from the housing wall.

5. The sensor, according to claim 1, in which a baffle extends into the housing from the housing wall.

6. The sensor, according to claim 1, in which a temperature sensor is located on a lower surface of the transparent window.

7. The sensor, according to claim 1, in which a baffle wall extends into the housing from the housing wall; and a temperature sensor is located on a lower surface of the transparent window.

8. The sensor, according to claim 1, in which the radiation emitter is a Light Emitting Diode (LED).

9. The sensor, according to claim 1, in which the radiation detector is a photo transistor or photo diode located adjacent to the radiation emitter so as to detect reflected radiation.

10. The sensor, according to claim 6, in which a controller is located in the housing and is connected to a variable resistor, the radiation detector, the radiation emitter and the temperature sensor.

11. The sensor, according to claim 6, in which a controller is located in the housing and is connected to a fixed resistor, the radiation detector, the radiation emitter and the temperature sensor.

12. The sensor, according to claim 1, in which the radiation detector is an integrated circuit having a photo transistor, a photo diode or a light dependent resister located adjacent to the radiation emitter so as to detect reflected radiation.

13. The sensor, according to claim 1, in which the reflective material is winter precipitation.

14. The sensor, according to claim 13, in which the winter precipitation is snow, sleet, frost, ice or ice pellets.

15. The sensor, according to claim 1, in which the reflective material is non-winter precipitation.

16. The sensor, according to claim 15, in which the non-winter precipitation is reflective liquids, dirt, or particulate material suspended in liquids.

17. The sensor, according to claim 1, is mounted for use on motorized transportation including trucks, cars, motor bikes, recreational vehicles, trains, or boats.

18. The sensor, according to claim 1, is mounted for use on solar panels and trough reflectors.

19. The sensor, according to claim 1, is mounted for use on sidewalks, driveways, walkways, roads, roofs, or infrastructure projects.

20. The sensor, according to claim 1, is mounted for use with greenhouses, atriums, windows, freezer glass doors, skylights; on planes, helicopters; food services, freezers/fridges, spacecraft, buildings; for landscaping such as grass and garden maintenance, crops; or for weather determination, climate, ecosystem preservation; or for medical applications and storage of tissues and cells, sterilizations; or for food preparation and preservation.

21. The sensor, according to claim 1, is used in solar applications for building materials including decking, walls or shingles.

\* \* \* \* \*